(12) United States Patent
Leal et al.

(10) Patent No.: US 11,518,951 B2
(45) Date of Patent: Dec. 6, 2022

(54) METHOD OF PRODUCING A FUEL ADDITIVE

(71) Applicants: SABIC Global Technologies B.V., Bergen op Zoom (NL); Saudi Arabian Oil Company, Dhahran (SA)

(72) Inventors: Guillermo Leal, Riyadh (SA); Naif Mohammed Al-Naddah Al-Otaibi, Riyadh (SA); Kareemuddin Mahaboob Shaik, Dhahran (SA); Mohammed Bismillah Ansari, Riyadh (SA); Vijay Dinkar Bodas, Riyahd (SA)

(73) Assignees: SABIC GLOBAL TECHNOLOGIES B.V., Bergen op Zoom (NL); SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/981,189

(22) PCT Filed: Mar. 18, 2019

(86) PCT No.: PCT/IB2019/052178
§ 371 (c)(1),
(2) Date: Sep. 15, 2020

(87) PCT Pub. No.: WO2019/180585
PCT Pub. Date: Sep. 26, 2019

(65) Prior Publication Data
US 2021/0024843 A1   Jan. 28, 2021

Related U.S. Application Data

(60) Provisional application No. 62/644,628, filed on Mar. 19, 2018.

(51) Int. Cl.
*C10L 1/16*     (2006.01)
*C07C 5/05*    (2006.01)
(Continued)

(52) U.S. Cl.
CPC .............. *C10L 1/1608* (2013.01); *C07C 5/05* (2013.01); *C07C 7/005* (2013.01); *C07C 7/04* (2013.01);
(Continued)

(58) Field of Classification Search
CPC .. C07C 29/04; C07C 5/05; C07C 7/13; C07C 11/08; C07C 11/09; C07C 31/12;
(Continued)

(56) References Cited

U.S. PATENT DOCUMENTS 3,061,654 A * 10/1962 Genshelmer .............. C07C 7/13
  585/820
3,797,690 A   3/1974 Taylor et al.
(Continued)

FOREIGN PATENT DOCUMENTS

CA    2018524 A1   12/1990
CN    1044804 C    8/1999
(Continued)

OTHER PUBLICATIONS

Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.
(Continued)

*Primary Examiner* — Latosha Hines
(74) *Attorney, Agent, or Firm* — Cantor Colburn LLP (57) ABSTRACT

A method of producing a fuel additive includes passing a feed stream comprising C4 hydrocarbons through a hydrogenation unit producing a hydrogenated stream; passing the hydrogenated stream through a distillation unit producing a first stream and a second stream; producing an isobutylene stream by passing the first stream through a molecular sieve unit; passing the isobutylene stream to a hydration unit as a
(Continued)

feedstock for the fuel additive; and forming the fuel additive in the hydration unit.

18 Claims, 1 Drawing Sheet

(51) Int. Cl.
    *C07C 7/00*     (2006.01)
    *C07C 7/04*     (2006.01)
    *C07C 7/13*     (2006.01)
    *C07C 29/04*    (2006.01)
    *C10L 10/10*    (2006.01)
    *C10L 1/182*    (2006.01)

(52) U.S. Cl.
    CPC ............... *C07C 7/13* (2013.01); *C07C 29/04* (2013.01); *C10L 1/1824* (2013.01); *C10L 10/10* (2013.01)

(58) Field of Classification Search
    CPC ... C07C 7/005; C07C 7/04; C10L 1/14; C10L 1/1608; C10L 1/1616; C10L 1/1824; C10L 10/10; C10G 2300/4081; C10G 2300/80; C10G 45/32; C10G 47/00; C10G 65/12; C10G 9/36
    See application file for complete search history.

(56) References Cited

U.S. PATENT DOCUMENTS

| | | |
|---|---|---|
| 3,849,082 A | 11/1974 | Kozlowski et al. |
| 3,912,463 A | 10/1975 | Kozlowski et al. |
| 4,324,936 A | 4/1982 | Mikulicz |
| 4,334,890 A | 6/1982 | Kochar et al. |
| 4,336,046 A | 6/1982 | Schorre et al. |
| 4,356,339 A | 10/1982 | Imaizumi et al. |
| 4,408,085 A | 10/1983 | Gottlieb et al. |
| 4,423,251 A | 12/1983 | Pujado et al. |
| 4,436,946 A | 3/1984 | Smitny |
| 4,455,445 A | 6/1984 | Neuzil et al. |
| 4,499,313 A | 2/1985 | Okumura et al. |
| 4,540,831 A | 9/1985 | Briggs |
| 4,773,968 A | 9/1988 | O'Connell et al. |
| 4,783,555 A | 11/1988 | Atkins |
| 4,797,133 A * | 1/1989 | Pujado .................. C10L 1/023 44/449 |
| 4,927,977 A | 5/1990 | Child et al. |
| 5,227,553 A | 7/1993 | Polanek et al. |
| 5,254,748 A | 10/1993 | Hensley et al. |
| 5,382,707 A | 1/1995 | Rubin et al. |
| 5,523,502 A | 6/1996 | Rubin |
| 5,563,299 A | 10/1996 | Paludetto et al. |
| 5,628,880 A | 5/1997 | Hearn et al. |
| 5,672,795 A | 9/1997 | Vora et al. |
| 5,877,365 A | 3/1999 | Chodorge et al. |
| 5,898,091 A | 4/1999 | Chodorge et al. |
| 5,955,640 A | 9/1999 | Paludetto et al. |
| 7,227,047 B2 | 6/2007 | Risch et al. |
| 7,459,593 B1 | 12/2008 | Krupa et al. |
| 7,473,812 B2 | 1/2009 | Peters et al. |
| 7,485,761 B2 | 2/2009 | Schindler et al. |
| 8,124,572 B2 | 2/2012 | Miller |
| 8,395,007 B2 | 3/2013 | Wright et al. |
| 8,999,013 B2 | 4/2015 | Xu et al. |
| 9,187,388 B2 | 11/2015 | Arjah et al. |
| 9,611,192 B2 | 4/2017 | Digiulio |
| 10,774,020 B2 | 9/2020 | Di Girolamo et al. |
| 2002/0169346 A1 | 11/2002 | Commereuc et al. |
| 2003/0158429 A1 | 8/2003 | Albiez et al. |
| 2004/0171891 A1 | 9/2004 | Scholz et al. |
| 2005/0107628 A1 | 5/2005 | Roper et al. |
| 2005/0288534 A1 | 12/2005 | Fernandez et al. |
| 2007/0149839 A1 | 6/2007 | Rix et al. |
| 2007/0265483 A1 | 11/2007 | Himelfarb |
| 2008/0146858 A1 | 6/2008 | Elomari et al. |
| 2008/0312481 A1 | 12/2008 | Leyshon |
| 2009/0193710 A1 | 8/2009 | Xiong et al. |
| 2011/0040133 A1 | 2/2011 | Vermeiren et al. |
| 2011/0230632 A1 | 9/2011 | Abhari |
| 2012/0117862 A1 | 5/2012 | Xu |
| 2012/0283492 A1* | 11/2012 | Dalemat ................. C10G 65/08 585/16 |
| 2013/0072732 A1 | 3/2013 | Breuil et al. |
| 2013/0104449 A1 | 5/2013 | Xu et al. |
| 2013/0172627 A1 | 7/2013 | Chewter et al. |
| 2013/0331620 A1 | 12/2013 | Abhari |
| 2014/0039226 A1 | 2/2014 | Xu et al. |
| 2014/0142350 A1 | 5/2014 | Weiner et al. |
| 2015/0225320 A1 | 8/2015 | Shaik et al. |
| 2015/0322181 A1 | 11/2015 | Kim et al. |
| 2016/0326079 A1 | 11/2016 | Lee et al. |
| 2017/0073289 A1 | 3/2017 | Leal et al. |
| 2017/0198231 A1 | 7/2017 | Xu et al. |
| 2017/0253540 A1 | 9/2017 | Hofel et al. |
| 2020/0157450 A1 | 5/2020 | Leal et al. |
| 2021/0002185 A1 | 1/2021 | Leal et al. |
| 2021/0024837 A1 | 1/2021 | Leal et al. |
| 2021/0155862 A1 | 5/2021 | Leal et al. |
| 2021/0171848 A1 | 6/2021 | Leal et al. |
| 2021/0214290 A1 | 7/2021 | Ansari et al. |
| 2021/0246088 A1 | 8/2021 | Leal et al. |

FOREIGN PATENT DOCUMENTS

| | | | |
|---|---|---|---|
| CN | 1506344 A | 6/2004 | |
| CN | 1736589 A | 2/2006 | |
| CN | 1990438 A * | 7/2007 | ............ C07C 11/08 |
| CN | 101279879 A | 10/2008 | |
| CN | 102070391 A | 5/2011 | |
| CN | 105585411 A | 5/2016 | |
| CN | 106608791 A | 5/2017 | |
| CN | 102372573 A | 3/2021 | |
| EP | 0063813 B1 | 11/1982 | |
| EP | 0102840 B1 | 3/1984 | |
| EP | 0253679 | 1/1988 | |
| EP | 0605822 A1 | 7/1994 | |
| GB | 1374368 | 11/1974 | |
| JP | S5920232 A | 2/1984 | |
| JP | 2010111596 A | 5/2010 | |
| RU | 2470905 C1 | 12/2012 | |
| WO | 9011268 | 10/1990 | |
| WO | 9732838 A1 | 9/1997 | |
| WO | 0043336 A1 | 7/2000 | |
| WO | 0146095 A1 | 6/2001 | |
| WO | 2006113191 A2 | 10/2006 | |
| WO | 2007024733 A2 | 3/2007 | |
| WO | 2012095744 A2 | 7/2012 | |
| WO | 2014153570 A2 | 9/2014 | |
| WO | 2014160825 A1 | 10/2014 | |
| WO | 2015089005 A1 | 6/2015 | |
| WO | 2015123026 A1 | 8/2015 | |
| WO | 2019207477 A1 | 10/2019 | |

OTHER PUBLICATIONS

Brockwell et al.; "Synthesize ethers"; Hydrocarbon Processing, vol. 70, No. 9; 1991; pp. 133-141.

International Search Report for International Application No. PCT/IB2019/052177; International Filing Date Mar. 18, 2019; dated Jun. 26, 2019; 3 pages.

International Search Report for International Application No. PCT/IB2019/053697; International Filing Date May 6, 2019; dated Aug. 28, 2019; 11 pages.

International Search Report for International Application No. PCT/IB2019/057784; International Filing Date Sep. 16, 2019; dated Jan. 7, 2020; 5 pages.

International Search Report for International Application No. PCT/US2019/026985; International Filing Date Apr. 11, 2019; dated May 27, 2019; 6 pages.

(56) References Cited

OTHER PUBLICATIONS

International Search Report for International Application No. PCT/US2019/028092; International Filing Date Apr. 18, 2019; dated Jun. 26, 2019; 6 pages.
International Search Report for International Application No. PCT/US2019/028099; International Filing Date Apr. 18, 2019; dated Jun. 26, 2019; 6 pages.
International Search Report; International Application No. PCT/IB2018/055647; International Filing Date: Jul. 27, 2018; dated Oct. 30, 2018; 6 pages.
Izquierdo et al.; "Equilibrium Constants for Methyl tert-Butyl Ether Liquid-Phas Synthesis"; J. Chem. Eng. Data, vol. 37; 1992; pp. 339-343.
Kalamaras et al.; "SuperButol—A novel high-octane gasoline blending component"; Fuel, vol. 195; 2017; pp. 165-173.
Streich et al.; "Secure the Best Benefits from C4 Hydrocarbon Processing—Part 1: Separation Sequences"; Hydrocarbon Processing: Process Engineering and Optimization; 2016; 6 pages.
Written Opinion for International Application No. PCT/IB2019/052177; International Filing Date Mar. 18, 2019; dated Jun. 26, 2019; 9 pages.
Written Opinion for International Application No. PCT/IB2019/053697; International Filing Date May 6, 2019; dated Aug. 28, 2019; 9 pages.
Written Opinion for International Application No. PCT/IB2019/057784; International Filing Date Sep. 16, 2019; dated Mailing Jan. 7, 2020; 7 pages.
Written Opinion for International Application No. PCT/US2019/026985; International Filing Date Apr. 11, 2019; dated May 27, 2019; 7 pages.
Written Opinion for International Application No. PCT/US2019/028092; International Filing Date Apr. 18, 2019; dated Jun. 26, 2019; 9 pages.
Written Opinion for International Application No. PCT/US2019/028099; International Filing Date Apr. 18, 2019; dated Jun. 26, 2019; 13 pages.
Written Opinion; International Application No. PCT/IB2018/055647; International Filing Date: Jul. 27, 2018; dated Oct. 30, 2018; 11 pages.
International Search Report for International Application No. PCT/IB2019/052178; International Filing Date Mar. 18, 2019; dated Jun. 26, 2019; 6 pages.
Written Opinion for International Application No. PCT/IB2019/052178; International Filing Date Mar. 18, 2019; dated Jun. 26, 2019; 9 pages.
International Search Report for International Application No. PCT/IB2019/059984; International Filing Date Nov. 20, 2019; dated Feb. 21, 2020; 5 pages.
Written Opinion for International Application No. PCT/IB2019/059984, International Filing Date Nov. 20, 2019; dated Feb. 21, 2020; 8 pages.
Bodas et al.; U.S. Appl. No. 17/292,261; entitled "Process and System for Producing Ethylene and at Least One of Butanol and an Alkyl Tert-Butyl Ether"; filed May 7, 2021.
International Search Report for International Application No. PCT/IB2020/051908; International Filing Date Mar. 2, 35020; dated May 29, 2020; 6 pages.
Leal et al. U.S. Appl. No. 17/436,753, entitled "Method of Producing a Fuel Additive", filed Sep. 7, 2021.
Written Opinion for International Application No. PCT/IB2020/051908; International Filing Date Mar. 5, 2020; dated May 29, 2020; 9 pages.
Fuel Additives Selection Guide: Types, Features, Applications, Engineering 360, 4 pages, obtained May 11, 2022, http://www.globalspec.com/learnmore/materials_chemicals_adhesives/industrial_oils_fluids/fuel_oil_fluid_additives (Year: 2022).
Indian Office Action for the Indian Application No. 202117040763; dated Aug. 30, 2022; 6 pages.

* cited by examiner

METHOD OF PRODUCING A FUEL ADDITIVE

CROSS REFERENCE TO RELATED APPLICATIONS

This application is a National Stage application of PCT/IB2019/052178, filed Mar. 18, 2019, which is incorporated herein by reference in its entirety, and which claims the benefit of U.S. Provisional Application No. 62/644,628, filed Mar. 19, 2018.

BACKGROUND

Commercial gasoline, which is fuel for internal combustion engines, is a refined petroleum product that is typically a mixture of hydrocarbons (base gasoline), additives, and blending agents. Additives and blending agents are added to the base gasoline to enhance the performance and the stability of gasoline, for example octane boosters.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline.

Hydrocarbon cracking processes are important conversion processes used in petroleum refineries. For example, fluid catalytic cracking (FCC) is widely used to convert the high-boiling, high-molecular weight hydrocarbon fractions of petroleum crude oils to more valuable gasoline, olefinic gases, and other products. Thermal cracking of naphtha and gas oil is also widely used in the petrochemical industry to produce a variety of olefins and aromatics. For example, hydrocarbon feed stocks can be mixed with steam and subjected to elevated temperatures (e.g., 700-900° C.) in a steam cracker furnace wherein the feed stock components are cracked into various fractions. The effluent of the steam cracker can contain a gaseous mixture of hydrocarbons, for example, saturated and unsaturated olefins and aromatics (C1-C35). The effluent can then be separated into individual olefins (for example, ethylene, propylene and C4's) and pyrolysis gasoline. Recycle streams of crude hydrocarbons are often formed as byproducts during these cracking processes.

The presence of isobutylene, butadiene, 1-butene, 2-butene, and other components within the crude hydrocarbon streams can allow for the formation of valuable alcohols and fuel additives. However, the conversion of crude hydrocarbon streams to fuel additive products can often be inefficient and costly. Furthermore, the final product specifications for such alcohols can be undesirable and can fail to meet market quality requirements. For example, alcohol products can have high levels of impurities, high Reid vapor pressures, e.g., greater than or equal to 13.79 kilopascals (kPa) (2.0 pounds per square inch (psi)), and low octane numbers, e.g., less than or equal to 82 Research Octane Number (RON), all of which correlate with poor product quality. Any improvement in these specifications and/or the efficiency of the process can provide a more valuable fuel additive product.

Thus, there is a need for an efficient method of producing fuel additives that can make use of crude hydrocarbon streams and produce final products with low impurities and high-performance specifications.

SUMMARY

Disclosed, in various embodiments, are methods of producing fuel additives.

A method of producing a fuel additive includes passing a feed stream comprising C4 hydrocarbons through a hydrogenation unit producing a hydrogenated stream; passing the hydrogenated stream through a distillation unit producing a first stream and a second stream; producing an isobutylene stream by passing the first stream through a molecular sieve unit; passing the isobutylene stream to a hydration unit as a feedstock for the fuel additive; and forming the fuel additive in the hydration unit.

A method of producing a fuel additive includes producing hydrogenated products by passing a feed stream comprising C4 hydrocarbons through a hydrogenation unit, wherein greater than or equal to 90% of any butadiene present in the feed stream is converted to 1-butene and/or 2-butene within the hydrogenation unit; passing the hydrogenated products through a distillation unit producing a first stream comprising isobutylene and isobutane and a second stream comprising n-butane, 1-butene, and 2-butene; producing an isobutylene stream having greater than or equal to 90% purity by passing the first stream through a molecular sieve unit having a pore size of 3 to 10; passing the isobutylene to a hydration reactor as a feedstock; withdrawing a 2-butene stream from the distillation unit, passing the 2-butene stream through a second hydrogenation unit producing a 1-butene stream, and passing the 1-butene stream to the hydration reactor as a feedstock; withdrawing a fuel additive product from the hydration reactor, wherein the fuel additive product comprises greater than or equal to 0.5% by weight trimethylpentane.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Disclosed herein is an efficient method of producing fuel additives that can make use of crude hydrocarbon streams and produce final products having low impurities and high-performance specifications. For example, the method disclosed herein can provide a unique sequence of unit operations that converts crude hydrocarbons into valuable fuel additives, such as alcohol fuel additives. This unique sequence can significantly improve the efficiency of the process, thereby reducing total capital costs. The final fuel additive products can have high levels of trimethylpentane, high octane numbers, and low Reid vapor pressures. For example, the final fuel additive products can have less than or equal to 50% by weight trimethylpentane, for example, less than or equal to 25% by weight trimethylpentane, for example, greater than or equal to 0.1% by weight trimethylpentane, for example, greater than or equal to 0.5% by weight trimethylpentane, for example, greater than or equal to 1.0% by weight trimethylpentane, for example, 0.1 to 50% by weight trimethylpentane. For example, the final fuel additive products can have an octane number of greater than 80, for example, greater than 85, for example, greater than 90. For example, the final fuel additive products can have Reid vapor pressures of less than or equal to 100 kilopascals (kPa), for example, less than or equal to 75 kPa, for example, less than or equal to 55 kPa, for example, less than or equal to 50 kPa, for example, 25 to 125 kPa, for example, 30 to 55 kPa. Any one or all of these properties can correlate with high performance and high market value. The method disclosed herein can also produce secondary products along with the fuel additive product. For example, ethylene and propylene products can be produced along with the fuel additive, thus maximizing the efficiency and productivity of the process.

The method disclosed herein can provide a process for producing a fuel additive with a minimal number of components. For example, the inclusion of a hydrogenation unit, for example, a selective hydrogenation unit, in the method can transform the butadiene components to 1-butene and 2-butene together with the utilization of isobutylene without the inclusion of a butadiene unit or a MTBE unit in the method. The method can produce fuel additives, for example, alcohol fuel additives, for example, C4 fuel additives, from mixed crude hydrocarbon feedstocks, for example, C4 hydrocarbons, from cracking units, such as steam cracking units with minimum capital expenditures and maximum production of the fuel additive with even further increased efficiency.

The method disclosed herein can provide a novel design for utilization and transformation of crude hydrocarbons from a cracking unit recycle stream as a feedstock to maximize production of the fuel additive. The method includes the use of selective hydrogenation units, and hydration units for the maximum production of the fuel additive. The method can include the use of molecular sieves to maximize the amount of isobutylene used as a feedstock to a hydration unit, which can assist in maximizing the amount of fuel additive that is produced.

The method of making a fuel additive herein can include passing a feed stream of crude hydrocarbons through a hydrogenation unit, for example, a selective hydrogenation unit. The crude C4 hydrocarbon feed stream can include C4 hydrocarbons. This hydrogenation unit can convert the butadiene present in the feed stream to 1-butene and 2-butene, forming a hydrogenated stream. The hydrogenated stream can then be passed through a distillation unit, which can separate the hydrogenated stream into component hydrocarbons. The reduction of butadiene and the maximization of butenes in the streams of this method can increase desirable product specifications of the fuel additive, such as the octane number. A first stream comprising isobutane and isobutylene can be withdrawn from the distillation unit and passed through a molecular sieve unit. The molecular sieve unit can isolate isobutylene. A second stream comprising 1-butene and 2-butene can also be withdrawn from the distillation unit. The isobutylene stream and the second stream (comprising butenes) can then be passed through a hydration unit to produce a fuel additive, for example, a fuel additive, for example, a mixed alcohols fuel additive, for example, a C4 alcohol fuel additive. Recycle streams from within the process can be used to produce ethylene and propylene as secondary products. Accordingly, the present process can maximize product quality for a fuel additive product while also producing additional secondary products in an efficient manner.

The method disclosed herein can include passing a feed stream through an olefin production unit, for example, a hydrocarbon cracking unit, for example, a catalytic and/or steam cracking unit, such that a source of the feed stream can include a product of an olefin cracking process and/or an olefin production process. The feed stream can comprise hydrocarbons, for example, C4 hydrocarbons. Additional hydrocarbons, for example, C2 and C3 hydrocarbons, can also be fed to the olefin production unit. The feed stream can then be withdrawn from the olefin production unit as a crude C4 hydrocarbon stream. The feed stream produced by the olefin production unit can comprise propylene, ethyl acetylene, vinyl acetylene, propadiene, 1,3-butadiene, 1,2-butadiene, isobutylene, cis-2-butene, trans-2-butene, 1-butene, isobutane, n-butane, propene, or a combination thereof. The total C4 olefin content of the feed stream, when withdrawn from a steam cracking unit, can be greater than or equal to 90% by weight and the feed stream can comprise greater than or equal to 15% by weight isobutylene. The total C4 olefin content of the process stream when withdrawn from a fluid catalytic cracking unit can be greater than or equal to 35% by weight and the feed stream can comprise saturated hydrocarbons in an amount of greater than or equal to 30% by weight. For example, feed stream can comprise isobutane and n-butane in a combined amount of greater than or equal to 30% by weight. For example, the total C4 content of the process stream when withdrawn from a fluid catalytic cracking unit can be 30 to 65% by weight. Isobutylene can be present in the feed stream in an amount of 10 to 25% by weight. Saturated hydrocarbons can be present in the feed stream in amount of 30 to 65% by weight.

The feed stream can then be passed through a hydrogenation unit, for example, a selective hydrogenation unit. For example, the hydrogenation unit can be a selective butadiene hydrogenation unit. The selective butadiene hydrogenation unit can selectively convert butadiene to 1-butene and 2-butene. The feed stream entering the hydrogenation unit can comprise less than or equal to 50% by weight butadiene, for example, less than or equal to 30% by weight, for example, less than or equal to 20% by weight. [The hydrogenation unit can convert butadiene present in the feed stream to 1-butene, cis-2-butene and trans-2-butene forming a hydrogenated stream. The conversion rate from butadiene to 1-butene, cis-2-butene and trans-2-butene can be greater than or equal to 85%, for example, greater than or equal to 90%, for example, greater than or equal to 95%. The hydrogenation unit can also convert propylene, methyl acetylene, and propadiene present in the process stream to their corresponding butenes. Tertiary butyl catechol and/or hydrogen can be added to the process stream prior to passing through the hydrogenation unit.

The hydrogenation unit can comprise multiple reactors in series, for example, the unit can comprise three reactor stages. The first two reactor stages can convert butadiene present in the feed stream to 1-butene to 2-butene. The first two reactor stages can comprise a hydrogenation catalyst, for example, a selective hydrogenation catalyst. For example, the hydrogenation catalyst can comprise palladium with an aluminum base. Examples of other catalysts can be used included, but are not limited to, platinum, rhodium, palladium, ruthenium, cobalt, nickel, copper, or a combination thereof. The catalyst can be the same for the first two reactor stages. Hydrogen can be injected into the feed stream prior to passing through the first reactor stage. In the third reactor stage, the final hydrogenation reaction of di-olefins to a mono-olefin can be achieved. In this stage, carbon monoxide can be injected to attenuate the catalyst and minimize the isomerization reaction from 1-butene to 2-butene. During normal operations, a recommended carbon monoxide injection rate can be 2 parts per million mole/mole of the feed rate to the third reactor. Operation conditions for the hydrogenation unit can be found in Table 1. A first stream can then be withdrawn from the hydrogenation unit. Temperature was measured in degrees Celsius (° C.), pressure in kilopascals (kPa) and pounds per square inch gauge (psig), along with butadiene (BD) content at the exit in each reactor stage

| Reactor | Temp ° C. | Pressure kPa (psig) | Catalyst | BD content at exit |
|---|---|---|---|---|
| 1st Reactor | 40-70 | 965-2758 (140-400) | Noble metal/Alumina | 7% |
| 2nd Reactor | 50-60 | 965-2758 (140-400) | Noble metal/Alumina | 1% |
| 3rd Reactor | 60-80 | 1724-1862 (250-270) | Noble metal/Alumina | <0.01% |

The hydrogenated stream can then be passed through a distillation unit, for example, a kinetic distillation unit. This distillation unit can separate the process stream into component hydrocarbons forming a first stream and a second stream. Operation conditions for the distillation unit can be 600 kPa to 1000 kPa overhead pressure and a reflux temperature of 35 to 50° C. For example, a first stream comprising isobutane and isobutylene can be withdrawn from the distillation unit and passed through a molecular sieve unit. The first stream can comprise greater than or equal to 90% by weight isobutane and/or isobutylene. The molecular sieve unit can isolate the isobutylene present in the first stream while filtering out other hydrocarbon components. The molecular sieve can comprise zeolite. Zeolites typically have a general formula of $M_{x/n}[(AlO_2)_x(SiO_2)_y].mH_2O$, where x, y, m and n are positive integers. For example, Zeolite-X has a formula of $Na_{88}Al_{88}Si_{104}O_{384}.220H_2O$. Exemplary zeolites include, but are not limited, FAU type zeolites, X, Y, MFI type such as ZSM-5, Silicalite-1, zeolite A, Ferririte, or a combination thereof. Molecular sieves can be loaded with π complexing adsorbents. The π complexing adsorbents can include a support material and a compound supported on the support material. The compound can include a metal nitrate. Exemplary metal nitrates can include, but are not limited to, $AgNO_3$, $CuNO_3$, $Cu(NO_3)_2$, $Fe(NO_3)_2$, or a combination thereof. The support materials can involve structured silicas, alumina, alumino silicates, titanosilicates, operating pressures of 345 to 1034 kPa (50 to 150 psig) and an operating temperature of 10 to 150° C. The separation of isobutane and isobutylene is obtained in molecular sieve by π complexing adsorbents which can bind with olefins, whereas the saturated hydrocarbon pass through due to difference in electron affinity. An isobutylene stream can then be withdrawn from the molecular sieve unit and passed through a hydration unit. The isobutylene stream can have a purity level greater than or equal to 90%, for example, greater than or equal to 95%, for example, greater than or equal to 99%. The pores of the molecular sieve can have a diameter of 1 nanometer to 15 nanometers, for example, 4 nanometers to 10 nanometers, and all ranges and values there between. A second stream comprising 1-butene and 2-butene can also be withdrawn from the distillation unit and passed directly to the hydration unit.

A temperature within the distillation unit can be 25° C. to 100° C., for example, 45° C. to 70° C. A pressure within the distillation unit can be 500 kiloPascals to 1500 kiloPascals, for example, 750 kiloPascals to 1200 kiloPascals, for example, 785 kiloPascals to 1175 kiloPascals.

The hydration unit can hydrate the isobutylene stream and the second stream (comprising butenes) to produce the fuel additive, for example, an alcohol fuel additive, for example, a mixed alcohols fuel additive, for example, a C4 alcohol fuel additive. The second stream entering the hydration unit can comprise less than or equal to 5% butadiene by weight, for example, less than or equal to 3% by weight, for example, less than or equal to 1% by weight. The fuel additive product can be withdrawn from the hydration unit via a product stream. Water can be fed to the hydration unit via a water stream. The hydration unit can comprise an oscillating baffle reactor, a fixed bed reactor, a membrane integrated reactor, isothermal multitubular reactor, or a combination thereof. The hydration unit can convert butene present in the process stream to butanol. For example, 17 to 99% of the butene present in the second stream can be converted to butanol within the hydration unit. The process stream can be contacted with water and a catalyst within the hydration unit. For example, the catalyst can comprise phosphoric acid, hypophosphorous acid, sulfonic resin, super acid resins, niobium oxide, or a combination thereof. Water and butene can be present within the hydration unit in a molar ratio of 1-15.0 mole of water to 1 mole of butene, for example, 10 moles of water to 1.0 mole of butene. A temperature within the hydration unit can be 30° C. to 250° C., for example, 100° C. to 200° C. A pressure within the hydration unit can be 500 kiloPascals to 20,000 kiloPascals, for example, 5000 kiloPascals to 10,000 kiloPascals, for example, 7500 kiloPascals.

The fuel additive product can comprise 2-butanol, tert-butyl alcohol, C4-dimer, or a combination thereof, for example, the C4-dimer can comprise di-isobutylene, 2,2,4 trimethylpentane, 2,3,3 trimethylpentane, or a combination thereof. The fuel additive product can comprise greater than or equal to 0.01% by weight trimethylpentane, for example, greater than or equal to 5.0% by weight, for example, greater than or equal to 10.0% by weight, for example, greater than or equal to 15% by weight, for example, greater than or equal to 20.0% by weight. An octane number of the fuel additive product can be greater than or equal to 80 according to the Anti-Knock Index, for example, greater than or equal to 85, for example, greater than or equal to 90, for example, greater than or equal to 93, for example, greater than or equal to 95.

The octane number is a standard measurement used to gage the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Anti-Knock Index is measured by adding the research octane number and the motor octane number and dividing by two, i.e., (RON+MON)/2. The Research Octane Number is determined by running the fuel in a test engine at a speed of 600 revolutions per minute with a variable compression ratio under controlled conditions, and comparing the results with those for mixtures of iso-octane and n-heptane. Motor Octane Number is determined by testing a similar test engine to that used in determining the Research Octane Number but at a speed of 900 revolutions per minute with a preheated fuel mixture, higher engine speed, and variable ignition timing. Depending on the composition, the Motor Octane Number can be about 8 to 12 octanes lower than the Research Octane Number. The research octane number can be greater than or equal to 88, for example, greater than or equal to 91, for example, greater than or equal to 93, greater than equal 95, greater than equal to 100. The motor octane number can be greater than or equal to 82, for example, greater than or equal to 89, for example, greater than or equal to 90. Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by ASTM D-323. The measures the vapor pressure of gasoline volatile crude oil, and other volatile petroleum products, except for liquefied petroleum gases. Reid vapor pressure is measured in kiloPascals and represents a relative pressure to atmospheric pressure since ASTM D-323 measures the gage pressure of the sample in a non-evacuated chamber. High levels of vaporization are desired for winter staring and operation and lower levels are desirable in avoiding vapor lock during summer heat. Fuel cannot be pumped when vapor is present in the fuel line and winter starting will be difficult when liquid gasoline in the combustion chambers has not vaporized. This means that the Reid vapor pressure is changed accordingly by oil producers seasonally to maintain gasoline engine reliability.

The Reid vapor pressure of the fuel additive product can be less than or equal to 55 kiloPascals, for example, 5 kiloPascals to 55 kiloPascals, for example, 5 kiloPascals to 40 kiloPascals. The Reid vapor pressure can vary during winter and summer conditions such that the pressure can be at the higher end of the values during the winter and at the lower end of the values during the summer.

A 2-butene stream can also be withdrawn from the distillation unit and passed through a second hydrogenation unit. The 2-butene stream can comprise n-butane, 1-butene and 2-butene. The second hydrogenation unit can convert 2-butene present in the 2-butene stream to 1-butene. Operating conditions for the second hydrogenation unit can include a pressure of 34 kPa to 105 kPa (5-15 bar) and a temperature of 180 to 300° C. A 1-butene stream can then be withdrawn from the second hydrogenation unit and recycled to the distillation unit. The 1-butene stream can comprise 1-butene and n-butane. A portion of the 1-butene stream can optionally be passed through a separation unit. A temperature within the distillation unit can be 25° C. to 100° C., for example, 45° C. to 70° C. A pressure within the distillation unit can be 500 kiloPascals to 1500 kiloPascals, for example, 750 kiloPascals to 1200 kiloPascals, for example, 785 kiloPascals to 1175 kiloPascals. The separation unit can separate and isolate 1-butene. A separated 1-butene stream can then be withdrawn from the separation unit and passed through the hydration unit.

A recycle stream, e.g., a hydrocarbon recycle stream, can be withdrawn from the hydration unit and recycled to the initial feed stream and/or the olefin production unit, such as a steam cracker unit. The recycle stream can comprise butene, isobutane, n-butane, isobutylene, or a combination thereof. The recycle stream can optionally be passed through a recycle hydrogenation unit prior to returning to the feed stream. The recycle hydrogenation unit can convert the 1-butene and 2-butene present in the recycle stream to n-butane and isobutane. For example, greater than or equal to 90% of any butene present in the hydrocarbon recycle stream can be converted to butane within the recycle hydrogenation unit.

Additional recycle streams can be withdrawn from within the process and used to produce ethylene and propylene as secondary products. For example, n-butane streams can be withdrawn from the distillation unit and/or the separation unit. An isobutane stream can also be withdrawn from the molecular sieve unit. These additional recycle streams can then be used to produce ethylene and propylene secondary products. For example, a metathesis unit can convert normal butylene and ethylene to polymer grade propylene via metathesis.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 1:
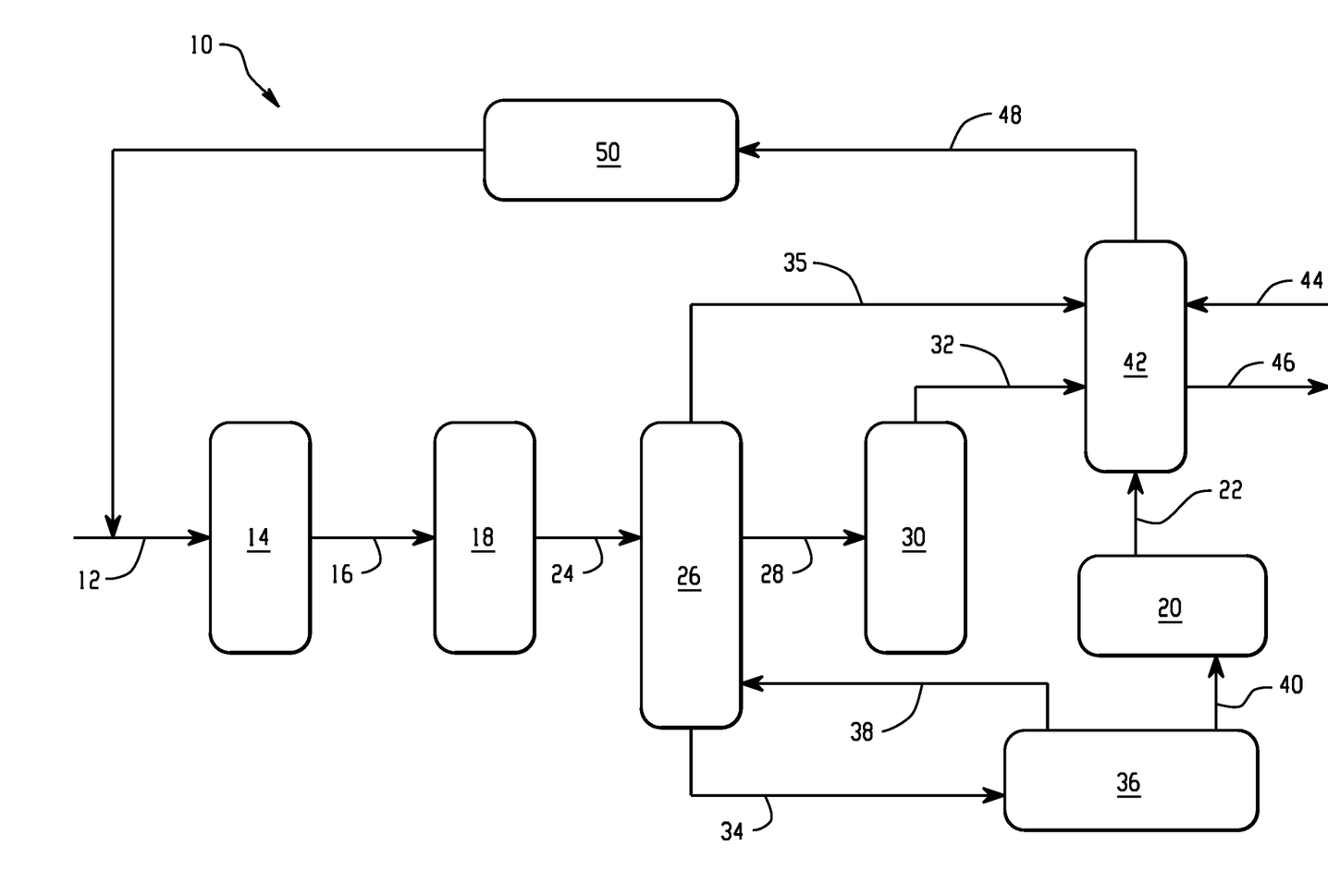
FIG. 1 is a schematic diagram representing a unit sequence for producing fuel additives.

Referring now to FIG. 1, this simplified schematic diagram represents a unit sequence 10 used in a method for producing fuel additives. The sequence 10 can include passing a raw material 12 comprising hydrocarbons through a hydrocarbon cracking unit 14. For example, the hydrocarbon cracking unit 14 can be a steam cracking and/or catalytic cracking unit.

The feed stream 16 can then be withdrawn from the cracking unit 14. The feed stream 16 can comprise crude hydrocarbons, for example, C4 hydrocarbons. The feed stream 16 can then be passed through a hydrogenation unit 18, for example, a selective hydrogenation unit. The hydrogenation unit 18 can be a selective butadiene hydrogenation unit and can comprise multiple reactors in series. This hydrogenation unit 18 can convert butadiene present in the feed stream 16 to 1-butene and 2-butene.

A hydrogenated stream 24 can then be withdrawn from the hydrogenation unit 18 and passed through a distillation unit 26. This distillation unit 26 can separate the hydrogenated stream 24 into component hydrocarbons. A first stream 28 comprising isobutane and isobutylene can be withdrawn from the distillation unit 26 and passed through a molecular sieve unit 30. The molecular sieve unit 30 can isolate the isobutylene present in the first stream 28 while filtering out other hydrocarbon components. An isobutylene stream 32 can then be withdrawn from the molecular sieve unit 30 and passed through a hydration unit 42. A second stream 35 comprising 1-butene and 2-butene can also be withdrawn from the distillation unit 26 and passed directly to the hydration unit 42.

The hydration unit 42 can hydrate the isobutylene stream 32 and the second stream 35 (comprising butenes) to produce the fuel additive. The fuel additive product 46 can be withdrawn from the hydration unit 42. Water can be fed to the hydration unit via stream 44.

A 2-butene stream 34 can also be withdrawn from the distillation unit 26 and passed through a second hydrogenation unit 36. The second hydrogenation unit 36 can convert 2-butene present in the stream 34 to 1-butene. A 1-butene stream 38 can then be withdrawn from the second hydrogenation unit 36 and recycled to the distillation unit 26. A portion of the 1-butene stream can optionally be passed through a separation unit 20 via stream 40. The separation unit 20 can separate and isolate 1-butene. A separated 1-butene stream 22 can then be withdrawn from the separation unit 20 and passed through the hydration unit 42.

A hydrocarbon recycle stream 48 can be withdrawn from the hydration unit 42 and recycled to the feed stream 12 and/or the cracking unit 14. The recycle stream 48 can be passed through a hydrogenation unit 50 prior to returning to the feed stream 12.

The methods disclosed herein include(s) at least the following aspects:

Aspect 1: A method of producing a fuel additive, comprising: passing a feed stream comprising C4 hydrocarbons through a hydrogenation unit producing a hydrogenated stream; passing the hydrogenated stream through a distillation unit producing a first stream and a second stream; producing an isobutylene stream by passing the first stream through a molecular sieve unit; passing the isobutylene stream to a hydration unit as a feedstock for the fuel additive; and forming the fuel additive in the hydration unit.

Aspect 2: The method of Aspect 1, wherein the feed stream comprises propylene, ethyl acetylene, vinyl acetylene, propadiene, 1,3-butadiene, 1,2-butadiene, isobutylene, cis-2-butene, trans-2-butene, 1-butene, isobutane, n-butane, propene, or a combination thereof.

Aspect 3: The method of any of the preceding aspects, wherein the first stream comprises isobutane and isobutylene.

Aspect 4: The method of any of the preceding aspects, wherein the second stream comprises 1-butene and 2-butene.

Aspect 5: The method of any of the preceding aspects, wherein greater than or equal to 85% by weight, preferably, greater than or equal to 90% by weight, more preferably, greater than or equal to 95% by weight of any butadiene present in the feed stream is converted to 1-butene and/or 2-butene within the hydrogenation unit.

Aspect 6: The method of any of the preceding aspects, further comprising passing a water stream through the hydration unit.

Aspect 7: The method of any of the preceding aspects, further comprising adding tertiary butyl catechol and/or hydrogen to the feed stream prior to passing through the hydrogenation unit.

Aspect 8: The method of any of the preceding aspects, further comprising withdrawing an isobutylene product from the isobutylene stream, wherein the isobutylene product has a purity of greater than or equal to 90%, preferably, greater than or equal to 95%, more preferably, greater than or equal to 99%.

Aspect 9: The method of any of the preceding aspects, further comprising withdrawing an n-butane stream from the distillation unit and recycling the n-butane stream back to the feed stream.

Aspect 10: The method of any of the preceding aspects, further comprising withdrawing an isobutane stream from the molecular sieve unit and recycling the isobutane stream back to the feed stream.

Aspect 11: The method of Aspect 10, further comprising passing the isobutane stream through a propylene unit and withdrawing a propylene product from the propylene unit.

Aspect 12: The method of any of the preceding aspects, further comprising withdrawing a 2-butene stream from the distillation unit, passing the 2-butene stream through a second hydrogenation unit producing a 1-butene stream, and recycling the 1-butene stream back to the distillation unit.

Aspect 13: The method of Aspect 12, further comprising passing at least a portion of the 1-butene stream through a separation unit and through the hydration unit.

Aspect 14: The method of any of the preceding aspects, wherein the hydration unit comprises an oscillating baffle reactor, a fixed bed reactor, a membrane integrated reactor, an isothermal multi-tubular reactor, or a combination thereof.

Aspect 15: The method of any of the preceding aspects, wherein greater than or equal to 0.01% of any butene present in the second stream is converted to butanol within the hydration unit.

Aspect 16: The method of any of the preceding aspects, further comprising withdrawing a fuel additive product from the hydration unit, wherein the fuel additive product comprises 2-butanol, tert-butyl alcohol, di-isobutene, or a combination thereof.

Aspect 17: The method of Aspect 16, wherein the fuel additive product comprises greater than or equal to 0.01% trimethylpentane.

Aspect 18: The method of Aspect 16, wherein an octane number of the fuel additive product is greater than or equal to 85 according to the Anti-Knock Index.

Aspect 19: The method of Aspect 16, wherein a Reid vapor pressure of the fuel additive product is less than or equal to less than or equal to 75 kiloPascals, preferably, less than or equal to 65 kiloPascals, preferably, less than or equal to 60, preferably less than or equal to 55 kiloPascals.

Aspect 20: A method of producing a fuel additive, comprising: producing hydrogenated products by passing a feed stream comprising C4 hydrocarbons through a hydrogenation unit, wherein greater than or equal to 90% of any butadiene present in the feed stream is converted to 1-butene and/or 2-butene within the hydrogenation unit; passing the hydrogenated products through a distillation unit producing a first stream comprising isobutylene and isobutane and a second stream comprising n-butane, 1-butene, and 2-butene; producing an isobutylene stream having greater than or equal to 90% purity by passing the first stream through a molecular sieve unit having a pore size of 3 to 10; passing the isobutylene to a hydration reactor as a feedstock; withdrawing a 2-butene stream from the distillation unit, passing the 2-butene stream through a second hydrogenation unit producing a 1-butene stream, and passing the 1-butene stream to the hydration reactor as a feedstock; and withdrawing a fuel additive product from the hydration reactor, wherein the fuel additive product comprises greater than or equal to 0.5% by weight trimethylpentane.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "+10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like. In a list of alternatively useable species, "a combination thereof" means that the combination can include a combination of at least one element of the list with one or more like elements not named Also, "at least one of" means that the list is inclusive of each element individually, as well as combinations of two or more elements of the list, and combinations of at least one element of the list with like elements not named.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing a fuel additive, comprising:
    passing a feed stream comprising C4 hydrocarbons through a hydrogenation unit producing a hydrogenated stream wherein the hydrogenation unit comprises multiple reactors in series wherein the reactors are operated at a temperature in the range of 40 to 80° C. and a pressure in the range of 140 to 400 psig wherein greater than or equal to 85% by weight of any butadiene present in the feed stream is converted to 1-butene and/or 2-butene within the hydrogenation unit;
    passing the hydrogenated stream through a distillation unit producing a first stream and a second stream;
    producing an isobutylene stream by passing the first stream through a molecular sieve unit;
    passing the isobutylene stream having a purity of greater than or equal to 90% to a hydration unit as a feedstock for the fuel additive; and
    forming the fuel additive in the hydration unit.

2. The method of claim 1, wherein the feed stream comprises at least one of propylene, ethyl acetylene, vinyl acetylene, propadiene, 1,3-butadiene, 1,2-butadiene, isobutylene, cis-2-butene, trans-2-butene, 1-butene, isobutane, n-butane, or propene.

3. The method of claim 1, wherein the first stream comprises isobutane and isobutylene.

4. The method of claim 1, wherein the second stream comprises 1-butene and 2-butene.

5. The method of claim 1, further comprising passing a water stream through the hydration unit.

6. The method of claim 1, further comprising adding tertiary butyl catechol and/or hydrogen to the feed stream prior to passing through the hydrogenation unit.

7. The method of claim 1, further comprising withdrawing an n-butane stream from the distillation unit and recycling the n-butane stream back to the feed stream.

8. The method of claim 1, further comprising withdrawing an isobutane stream from the molecular sieve unit and recycling the isobutane stream back to the feed stream.

9. The method of claim 8, further comprising passing the isobutane stream through a propylene unit and withdrawing a propylene product from the propylene unit.

10. A method of producing a fuel additive, comprising:
    passing a feed stream comprising C4 hydrocarbons through a hydrogenation unit producing a hydrogenated stream wherein the hydrogenation unit comprises multiple reactors in series wherein the reactors are operated at a temperature in the range of 40 to 80° C. and a pressure in the range of 140 to 400 psig;
    passing the hydrogenated stream through a distillation unit producing a first stream and a second stream;
    withdrawing a 2-butene stream from the distillation unit, passing the 2-butene stream through a second hydrogenation unit producing a 1-butene stream, and recycling the 1-butene stream back to the distillation unit;
    producing an isobutylene stream by passing the first stream through a molecular sieve unit;
    passing the isobutylene stream having a purity of greater than or equal to 90% to a hydration unit as a feedstock for the fuel additive; and
    forming the fuel additive in the hydration unit.

11. The method of claim 10, further comprising passing at least a portion of the 1-butene stream through a separation unit and through the hydration unit.

12. The method of claim 1, wherein the hydration unit comprises at least one of an oscillating baffle reactor, a fixed bed reactor, a membrane integrated reactor, or an isothermal multi-tubular reactor.

13. The method of claim 1, wherein greater than or equal to 0.01% of any butene present in the second stream is converted to butanol within the hydration unit.

14. The method of claim 1, further comprising withdrawing a fuel additive product from the hydration unit, wherein the fuel additive product comprises at least one of 2-butanol, tert-butyl alcohol, or di-isobutene.

15. The method of claim 14, wherein the fuel additive product comprises greater than or equal to 0.01% trimethylpentane.

16. The method of claim 14, wherein an octane number of the fuel additive product is greater than or equal to 85 according to the Anti-Knock Index.

17. The method of claim 14, wherein a Reid vapor pressure of the fuel additive product is less than or equal to 75 kiloPascals.

18. A method of producing a fuel additive, comprising:
producing hydrogenated products by passing a feed stream comprising C4 hydrocarbons through a hydrogenation unit, wherein greater than or equal to 90% of any butadiene present in the feed stream is converted to 1-butene and/or 2-butene within the hydrogenation unit;
passing the hydrogenated products through a distillation unit producing a first stream comprising isobutylene and isobutane and a second stream comprising n-butane, 1-butene, and 2-butene;
producing an isobutylene stream having greater than or equal to 90% purity by passing the first stream through a molecular sieve unit having a pore size of 3 to 10;
passing the isobutylene to a hydration reactor as a feedstock;
withdrawing a 2-butene stream from the distillation unit, passing the 2-butene stream through a second hydrogenation unit producing a 1-butene stream, and passing the 1-butene stream to the hydration reactor as a feedstock; and
withdrawing a fuel additive product from the hydration reactor, wherein the fuel additive product comprises greater than or equal to 0.5% by weight trimethylpentane.

* * * * *